United States Patent [19]

Mendell

[11] 4,098,277

[45] Jul. 4, 1978

[54] FITTED, INTEGRALLY MOLDED DEVICE FOR STIMULATING AURICULAR ACUPUNCTURE POINTS AND METHOD OF MAKING THE DEVICE

[76] Inventor: Sherwin Mendell, 2001 W. North Ave., Chicago, Ill. 60647

[21] Appl. No.: 763,411

[22] Filed: Jan. 28, 1977

[51] Int. Cl.$^2$ ......................... A61B 17/00; B29C 1/02; B29C 1/14

[52] U.S. Cl. ............................ 128/303 R; 128/329 A; 264/132; 264/222; 264/DIG. 30

[58] Field of Search ............... 264/222, DIG. 30, 132; 128/303 R, 329 A, 24 R, 24.2, 24.3, 151, 152; 179/107 E, 107 BC; 181/130–135

[56] References Cited

U.S. PATENT DOCUMENTS

| | | | |
|---|---|---|---|
| 1,755,775 | 4/1930 | Dunn | 264/DIG. 30 |
| 1,971,630 | 8/1934 | Suchorzynski | 179/107 BC |
| 3,923,064 | 12/1975 | Lenpold | 128/329 A |

*Primary Examiner*—James B. Lowe

[57] ABSTRACT

A method is provided for making a device for selectively applying pressure to discrete selected acupuncture pressure points on the auricular surface of the ear without penetrating skin. The selected acupuncture points are first marked with a marking substance, and then an impression is made by inserting malleable material into the ear. When the impression is removed from the ear, it has a surface which is complementary to the auricular surface and is marked by the marking substance to identify the selected acupuncture points. Projections are provided to the surface of the impression, and a mold is then formed from the projection bearing impression. The mold is filled with a moldable substance, which is hardened; and thereafter removed from the mold and polished as the device of the present invention. This device is preferably polished, provided with an earhole to allow unimpeded hearing, and may be worn in fitted, self-retaining pressure on the selected acupuncture points.

13 Claims, 2 Drawing Figures

FITTED, INTEGRALLY MOLDED DEVICE FOR STIMULATING AURICULAR ACUPUNCTURE POINTS AND METHOD OF MAKING THE DEVICE

BACKGROUND OF THE INVENTION

This invention relates to a method for forming a device for selectively applying pressure to discrete selected auricular acupuncture pressure points without penetrating the skin.

Recently, there has been a renewed interest in the ancient oriental practice of using acupuncture techniques to cure a variety of illnesses and other disorders. Generally, the practice of acupuncture involves inserting fine needles in predetermined locations on the body. The size of the needle and the location of the points on the body into which the needle is to be inserted (hereinafter referred to as "acupuncture points") depends upon the illness or disorder which is desired to be treated.

Many acupuncture points which are useful for treating a wide variety of illnesses and disorders are located on the surface of the ear. These points are identified in *Acupuncture*, by Czaplicki, on pp. 134–137, and may be stimulated by the usual acupuncture needles. However, whenever it is desired to stimulate the acupuncture points with acupuncture needles, the stimulation must be carried out by a physician trained in the art of acupuncture. In order to make acupuncture stimulation more readily available to the general public, those skilled in the art have been searching for methods for stimulating acupuncture points which can be carried out in the absence of a trained physician.

One proposed method has involved the insertion of staples into acupuncture points on the ear by a trained acupuncture practitioner. Proponents of this method maintain that the staples may be left in the ear for a considerable length of time. The advantage of this method is that whenever it is desired to stimulate the acupuncture point, a person having such staples inserted in his ear may simply manipulate the staples in order to obtain the desired effect. A serious drawback to this method is that the staples tend to cause infection to the skin of the ear at the points of insertion, may be painful to the patient, and may cause scarring.

In order to provide readily available access to acupuncture therapy without encountering the problems involved in puncturing the skin, it has also been proposed to apply tiny steel balls adhered to adhesive squares to acupuncture points on various places on the body. These steel balls are sold under the trade name Acu-Aids by Ionlab, Inc., Van Nuys, California. Although these Acu-Aids are suitable for application to acupuncture points on the body, they are not suitable for application to acupuncture points in the ear because there are a large number of acupuncture points crowded together in the relatively small auricular surface of the ear. Also, they may fall out, wash off, or otherwise move out of position, thus losing their desired effect or stimulating the wrong point.

Another method for stimulating auricular acupuncture points has been proposed by Francis J. McCall, and is commercially marketed as "Auricular Acu Mold Pressure Therapy". According to this method as treatment, a molded-pellet-bearing model of a patient's auricular cavity is used to stimulate acupuncture points. Generally, this model is made by forming an impression of the auricular surface of the ear, selecting the acupuncture points it is desired to stimulate, forming a mold from the impression of the ear, and filling the mold with a substance to form a model of the impression of the auricular surface of the patient's ear. Pellets are then set in the surface of the model on selected acupuncture points, which are determined by comparison of the surface of the model with charts which identify the known points of acupuncture action.

There are two obvious disadvantages of this method. One is that the location of acupuncture points on the ears of different people may differ slightly. Thus, the margin of error in placement of the pellets on the model may be greater than is desired. Another problem is that the pellets embedded on the surface are susceptible to being dislodged from the model if it is dropped or otherwise mishandled.

SUMMARY OF THE INVENTION

The present invention contemplates an improved method for forming a device for selectively applying pressure to discrete selected auricular acupuncture pressure points without penetrating skin. The method comprises marking selected acupuncture points on the auricular surface of the ear by depositing thereon a transferable marking substance. Next an impression is made of the auricular surface of the ear by impressing on the auricular surface a malleable material capable of being marked by contact with the marking substance deposited on the selected acupuncture points, and thereafter applying pressure to the malleable material to form a surface of complementary configuration to the auricular surface, the points on the complementary surface of the malleable material opposite the marked pressure points being marked by the marking substance. Next, the marked impression is removed from the ear and projections are supplied to the marked points on the complementary surface of the impression to form a projection-bearing surface which is used to form a mold having a molding surface complementary to the projection-bearing surface of the impression. The mold is then filled with a moldable substance capable of forming solid mass in the mold, which solid mass has a surface substantially identical to the surface of the projection-bearing impression. The moldable substance is thereafter hardened to form a model or device having a surface area complementary to the auricular surface of the ear, and having generally blunt projections located in correspondence with the selected acupuncture pressure points. Finally, the model is removed from the mold, and is preferably polished.

This novel process produces a novel, self-retaining device or model for stimulating the acupuncture points. The device has a surface generally conformable with the auricular surface of the human ear, with the surface of the device having one or more projections disposed thereon in an arrangement such that when the device is in fitted, self-retaining position in the ear, the projections exert stimulating pressure on one or more selected acupuncture points without penetrating the skin of the ear.

Devices made in accordance with this method have several advantages over the models used in prior art techniques discussed above. First, because the impression is made with a malleable material sensitive to the marking material used to pre-mark the acupuncture points on the auricular surface, the surface of the impression complementary to the auricular surface of the ear bears marks which make it possible to accurately locate the blunt projections on the surface of the impression, so that the projections in the finished device will accurately correspond to the auricular acupuncture points. Second, the projections on the surface of the self-retaining device of this invention are integrally molded parts of the device, as opposed to the embedded particles used in the previously discussed prior art techniques, and thus, are less likely to break off or fall out.

Other advantages of this method will become apparent from the following detailed description of the invention.

THE DRAWINGS

FIG. 1 is a diagram showing the auricular surface of a ear and identifying some of the acupuncture points thereon; and FIG. 2 is a plan view of a device of the present invention.

DETAILED DESCRIPTION

Figure 1:
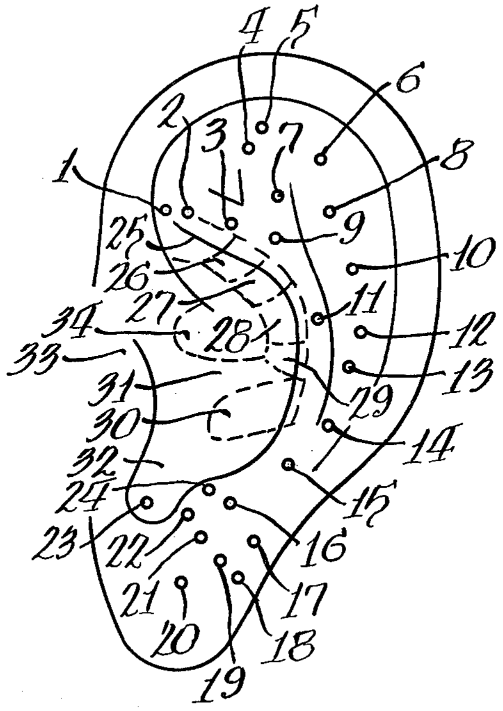

FIG. 1 is a diagrammatic view of an ear which shows the location of some of the major acupuncture points on the auricular surface. When the term auricular surface is used in this application, it is intended to include the surface of the ear as shown in FIG. 1.

According to the disclosure in *Acupuncture,* by Czaplicki, when any one of the enumerated points on the ear shown in FIG. 1 are stimulated by acupuncture means, such stimulation will result in a beneficial effect to the corresponding point on a patient's body. Some of the parts of the body which respond to acupuncture pressure on the enumerated points on the ear of FIG. 1 are set out in Table I below:

Table I

| | |
|---|---|
| 1. Vagina | 18. Cheek (Area below chin) |
| 2. Lower Trunk | 19. Manidble |
| 3. Hips-Gluteal Muscle | 20. Eyes |
| 4. Heels | 21. Maxilae |
| 5. Toes | 22. Forehead |
| 6. Fingers | 23. Thyroid Gland |
| 7. Knee | 24. Brain |
| 8. Wrist | 25. Bladder |
| 9. Abdomen | 26. Kidney |
| 10. Forearm | 27. Gall Bladder |
| 11. Chest | 28. Liver |
| 12. Shoulder | 29. Spleen |
| 13. Shoulder (Humerus) | 30. Heart |
| 14. Acromio-Cladicular | 31. Lung |
| 15. Neck | 32. Throat |
| 16. Sub-occiput | 33. Inside Nose |
| 17. Cheek (area chin) | 34. Mouth |

In the practice of acupuncture, it is important to accurately locate the acupuncture points illustrated in FIG. 1 on the patient's ear. Although auricular acupuncture points may be located by comparison with a chart, such as that shown in FIG. 1, the exact location of these points may vary from person to person. However, the location of any particular point on a person may be pinpointed using a meridian detector such as that which is made by Lycee Trading Corporation, East Northport, N.Y. Basically, a meridian detector is an electronic device having a probe supplied with a small amount of current which is connected to a microammeter for measuring differences in the probe current. By examining an ear with such a probe, a skilled acupuncture practitioner can accurately determine the location of the acupuncture points which are to be stimulated. Such meridian detectors and their use are well known to those skilled in the art of acupuncture.

In carrying out the method of the present invention, auricular acupuncture points are selected in accordance with the disease or disorder of the patient which is desired to be treated, are preferably located with a meridian acupuncture point detector or similar device. The selected acupuncture points are marked on the auricular surface by depositing on the surface a suitable transferable marking substance, such as indelible ink, indelible pencil, or any other marking substance which is not absorbed by the skin, but which can be transferred to a malleable, impression forming material by contact with it.

After the acupuncture points are marked with the transferable marking substance, an impression is formed of the auricular surface of the ear by impressing on the auricular surface a malleable material capable of being marked by contact with the marking substance deposited on the selected acupuncture points. Enough malleable material is used to partially fill the auricular cavity, which cavity is defined by the auricular surface containing the auricular acupuncture points shown in FIG. 1. Sufficient pressure is then applied to the malleable material to form a surface of complementary configuration to the auricular surface, and the points on the complementary surface of the malleable material contacting the marked pressure points are marked by the marking substance. One suitable material for forming the impression is manufactured by the Zenith Hearing Aid Corporation as an ear mold impression and liquid. Another suitable impression material is alginate, which is an insoluble, colloidal salt of alginic acid and is obtained from brown marine algae. Alginate is commonly used in dentistry to make models of teeth, and has excellent properties for such use since it is pliable when wet but is hard when dry.

When the malleable material is removed from the auricular cavity, the surface having a complementary configuration to the auricular surface retains its shape and carries marks on the complementary surface which correspond to the selected acupuncture points. Projections are then supplied to the marked points on the complementary surface of the malleable material to form a projection-bearing surface on the impression. Suitably, these projections are sufficiently pointed to stimulate a single selected acupuncture point, but are not pointed enough to puncture the skin. A suitable method for supplying the blunt projections to the surface of the impression is to insert pins into the material at the marked points on the surface so that the pin heads of varying selected shapes and sizes protrude from the surface. The length of the pin and the depth to which it is inserted into the impression is dependent upon the amount of pressure desired to be exerted on the selected acupuncture point. In addition to pins, other similar objects having points may also be used. The only limiting factor is that the projections should be sized to apply pressure to a single acupuncture pressure response point in the ear. Thus, the size of any projection will be determined by the location of the acupuncture pressure point as well as the relative location of the next adjacent acupuncture pressure point.

After the impression is supplied with the projections, it is used to form a mold having a molding surface complementary to the projection-bearing surface of the impression. Such a mold can be suitably formed by placing the projection-bearing impression in semi-solid plaster of paris, hardening the plaster of paris, and then removing the projection-bearing impression therefrom. The plaster of paris mold will then have a surface which is complementary to the projection-bearing surface of the impression. In addition to plaster of paris, other suitable mold forming materials may also be used, and such materials are well known to those skilled in the art.

The mold formed from the impression is then filled with a moldable substance capable of forming a solid mass in the mold, which solid mass has a surface substantially identical to the surface of the projection-bearing impression. One useful molding substance for filling the mold is an acrylic resin such as Lucite, which is manufactured by DuPont. It is of particular advantage to use Lucite, because Lucite hardens to form a device which is generally clear and attractive, and because of its clarity, is less apparent to an observer when worn. Also, Lucite may be colored to give it flesh tones or other colors according to the desire of the wearer.

The moldable substance in the mold is finally hardened to form a solid device or model having a surface generally complementary to the auricular surface, and having projections located in correspondence with the selected acupuncture points. Once the device has hardened, it is removed from the mold and is preferably rubbed or buffed to give it a smooth outer surface.

Figure 2:
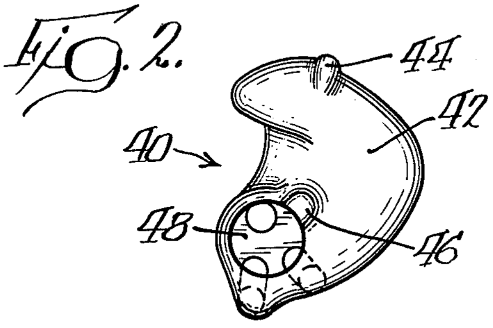

An embodiment of the device formed by the method of the present invention is shown in FIG. 2. It is a fitted, self-retaining integral device 40 for stimulating auricular acupuncture points. It has a surface 42 generally conformable with the auricular surface of the human ear from which the impression was made. The surface of the device has one or more generally blunt projections 44 and 46 disposed thereon and integral therewith in an arrangement such that when a device is in fitted, self-retaining disposition in an ear, each projection exerts stimulating pressure on a selected acupuncture point without penetrating the skin of the ear.

As an additional step to the novel method disclosed herein, the device 40 may also be provided with at least one hearing canal 48 in the area which is situated opposite the ear canal when it is disposed in fitted relationship in the auricular cavity. This allows a patient to wear the acupuncture pressure-point stimulating device 40 in his ear without impairing his hearing.

This invention has been described in terms of a preferred embodiment by way of illustration and not limitation. Other preferred embodiments are also contemplated and these embodiments are within the scope of the following claims.

I claim:

1. A method for forming a device for selectively applying pressure to discrete selected auricular acupuncture pressure points without penetrating skin, comprising:

marking selected acupuncture points on the auricular surface by depositing thereon a transferable marking substance;

forming an impression of the auricular surface of the ear by impressing on the auricular surface a malleable material capable of being marked by contact with the marking substance deposited on the selected acupuncture points, and applying pressure to the malleable material to form a surface of complementary configuration to the auricular surface, the points on the complementary surface of the malleable material contacting the marked pressure points being marked by the marking substance;

removing the marked impression from the auricular surface and supplying projections to the marked points on the complementary surface to form a projection-bearing surface;

forming a mold having a molding surface complementary to the projection-bearing surface of the impression;

filling the mold with a moldable substance;

hardening the moldable substance to form a solid device having a surface generally complementary to the auricular surface and having projections located in correspondence with the selected acupuncture pressure points; and removing the solid device from the mold.

2. A method in accordance with claim 1 wherein at least one hearing canal is provided in the area of the solid device which is situated opposite the ear canal when the device is disposed in fitted relationship in the auricular cavity.

3. The method of claim 1 wherein the malleable material is a thermoplastic substance.

4. The method of claim 1 wherein the liquid substance with which the mold is filled is an acrylic resin.

5. The method of claim 1 wherein the mold is formed by placing the projection-bearing impression in semisolid plaster of paris, hardening the plaster of paris, and removing the projection-bearing impression therefrom.

6. The method of claim 1 wherein the marking substance is ink.

7. The method of claim 1 wherein each projection is sized to apply pressure to a single acupuncture point on the auricular surface.

8. The method of claim 1 wherein the moldable substance is capable of forming a solid mass in the mold, which solid mass has a surface substantially identical to the surface of the projection bearing impression.

9. A method for forming a device for selectively applying pressure to discreet selected auricular acupuncture pressure points without penetrating skin, comprising:

marking selected acupuncture points on the auricular surface by depositing thereon a transferable marking substance:

forming an impression of the auricular cavity of the ear, by impressing on the auricular surface of the ear a malleable material, and applying pressure to the malleable material to form a surface of complementary configuration to the auricular surface, the points on the complementary configuration to the auricular surface, the points on the complementary surface of the malleable material contacting the marked pressure points being marked by the marking substance;

removing the marked impression from the auricular cavity and supplying projections to the marked points on the surface of the impression complementary to the auricular surface to form a projection-bearing surface;

forming a mold having a molding surface complementary to the projection-bearing surface of the impression;

filling the mold with a moldable substance capable of forming a solid mass in the mold, which solid mass has a surface substantially identical to the surface of the projection-bearing impression;

hardening the moldable substance to form a solid device having a surface generally complementary to the auricular surface and having projections located in correspondence with the selected acupuncture pressure points; and, removing the solid device from the mold.

10. A fitted, self-retaining integrally molded device for stimulating auricular acupuncture points, (a) the device having a surface generally conformable with the auricular surface of a human ear;

(b) the surface of the device having one or more integrally molded projections disposed thereon in an arrangement such that when the device is in fitted, self-retaining disposition in an ear, each projection exerts stimulating pressure on a selected acupuncture point without penetrating the skin of the ear.

11. The device in accordance with claim 10 wherein at least one hearing canal is provided in the area of the device which is situated opposite the ear canal when the device is disposed in fitted relationship in the auricular cavity.

12. The product of the process of claim 1.

13. The product of the process of claim 9.

* * * * *